(12) United States Patent
Saito et al.

(10) Patent No.: US 10,940,229 B2
(45) Date of Patent: Mar. 9, 2021

(54) MATERIAL FOR ADHESION PREVENTION

(71) Applicants: Toray Industries, Inc., Tokyo (JP); Nanotheta Co., Ltd., Tokyo (JP)

(72) Inventors: Akihiro Saito, Otsu (JP); Megumi Nakanishi, Otsu (JP); Kazuhiro Tanahashi, Otsu (JP); Toru Arakane, Tokyo (JP); Motonori Hochi, Otsu (JP); Ai Suzuki, Otsu (JP); Koji Okabayashi, Tokyo (JP); Shinji Takeoka, Tokyo (JP); Toshinori Fujie, Tokyo (JP); Yuya Ishiduka, Tokyo (JP); Shinya Ohtsubo, Tokyo (JP)

(73) Assignees: Toray Industries, Inc., Tokyo (JP); Nanotheta Co., Ltd., Tokyo (JP)

(*) Notice: Subject to any disclaimer, the term of this patent is extended or adjusted under 35 U.S.C. 154(b) by 0 days.

(21) Appl. No.: 16/335,082

(22) PCT Filed: Sep. 29, 2017

(86) PCT No.: PCT/JP2017/035402
§ 371 (c)(1),
(2) Date: Mar. 20, 2019

(87) PCT Pub. No.: WO2018/062464
PCT Pub. Date: Apr. 5, 2018

(65) Prior Publication Data
US 2019/0216971 A1 Jul. 18, 2019

(30) Foreign Application Priority Data
Sep. 30, 2016 (JP) .............................. JP2016-194699

(51) Int. Cl.
*A61L 15/26* (2006.01)
*A61L 31/14* (2006.01)
(Continued)

(52) U.S. Cl.
CPC .............. *A61L 15/26* (2013.01); *A61L 15/28* (2013.01); *A61L 15/64* (2013.01); *A61L 31/06* (2013.01);
(Continued)

(58) Field of Classification Search
CPC combination set(s) only.
See application file for complete search history.

(56) References Cited

U.S. PATENT DOCUMENTS 10,119,000 B2 * 11/2018 Hochi ..................... A61L 15/28
2012/0301515 A1 11/2012 Tani et al.
(Continued)

FOREIGN PATENT DOCUMENTS

JP 2014-140978 A 8/2014
WO 2011/081162 A1 7/2011
(Continued)

OTHER PUBLICATIONS

Hwal Suh et al., "Evaluation of Tissue Adhesion Preventive Surface Modified Natural and Synthetic Polymeric Materials," Materials Science Forum, vols. 426-432, 2003, pp. 3255-3260 (Abstract only).
(Continued)

*Primary Examiner* — Celeste A Roney
(74) *Attorney, Agent, or Firm* — DLA Piper LLP (US)

(57) ABSTRACT

A material for adhesion prevention can be adhered to biological tissue with certainty and has improved tissue adhesiveness and biodegradability. Such material for adhesion prevention is composed of: a 1- to 1,000-μm-thick water-soluble support layer comprising a water-soluble polymer; and a 1- to 1,000-μm-thick adhesion prevention layer comprising a biodegradable polymer. The biodegradable polymer has a structure in which a branched polyalkylene glycol comprising 3 to 8 terminal hydroxyl groups
(Continued)

per molecule is bound to a polyhydroxy alkanoic acid, and a mass ratio of the branched polyalkylene glycol relative to the total mass is 1% to 30%.

4 Claims, 2 Drawing Sheets

(51) Int. Cl.
    *A61L 31/12*     (2006.01)
    *A61L 31/06*     (2006.01)
    *A61L 15/64*     (2006.01)
    *A61L 15/28*     (2006.01)
    *A61P 41/00*     (2006.01)
    *C08G 65/26*     (2006.01)
    *C08L 5/08*     (2006.01)

(52) U.S. Cl.
    CPC ............. *A61L 31/12* (2013.01); *A61L 31/125* (2013.01); *A61L 31/14* (2013.01); *A61L 31/148* (2013.01); *A61P 41/00* (2018.01); *A61L 31/145* (2013.01); *C08G 65/2615* (2013.01); *C08L 5/08* (2013.01)

(56) References Cited

U.S. PATENT DOCUMENTS

| | | |
|---|---|---|
| 2016/0002422 A1 | 1/2016 | Hochi et al. |
| 2017/0072669 A1 | 3/2017 | Sekido et al. |
| 2017/0348465 A1 | 12/2017 | Saito et al. |

FOREIGN PATENT DOCUMENTS

| | | |
|---|---|---|
| WO | 2014/141983 A1 | 9/2014 |
| WO | 2015/194616 A1 | 12/2015 |
| WO | 2016/204266 A1 | 12/2016 |

OTHER PUBLICATIONS

Koji Nagahama et al., "Synthesis of Star-shaped 8 arms Poly(ethylene glycol)-Poly($_L$-lactide) Block Copolymer and Physicochemical Properties of Its Solution Cast Film as Soft Biomaterial," Polymer Journal, vol. 38, No. 8, 2006, pp. 852-860.

Martina Kessler et al., "Application of Linear and Branched Poly(Ethylene Glycol)-Poly(Lactide) Block Copolymers for the Preparation of Films and Solution Electrospun Meshes," Macromolecula Bioscience, vol. 16, Mar. 2016, pp. 441-450.

\* cited by examiner

MATERIAL FOR ADHESION PREVENTION

TECHNICAL FIELD

This disclosure relates to a material for adhesion prevention used to suppress adhesion occurring after surgery or other occasions.

BACKGROUND

Injury, bleeding, inflammation and the like that occur on the body tissue surface during surgery could cause adhesion between the body tissue and tissue in the vicinity thereof. Since adhesion prevents normal actions of organs, adhesion becomes problematic as a postsurgical complication. When adhesion occurs between an intestinal tract and an abdominal wall or between intestinal tracts in the abdominal cavity upon open surgery, for example, flow ability in the intestinal tract is deteriorated, and enterostasis (i.e., adhesive intestinal obstruction) occurs occasionally. Thus, another operation often becomes necessary.

Therefore, various types of materials for adhesion prevention have been developed and used. Materials for adhesion prevention currently used are aimed at adhesion prevention by physically shielding the site of injury from the tissue in the vicinity thereof until the damaged tissue is healed. It is preferable that materials for adhesion prevention should be dissolved or degraded within 1 to 4 weeks during which healing of injury is completed in the body. This is because, if such materials are retained for a long period of time in the body, the onset of fever and inflammation caused by the foreign body reaction may be continued.

As conventional materials for adhesion prevention, materials prepared with the use of a water-soluble polymer such as pullulan have been known. For example, WO 2011/081162 discloses a material for adhesion prevention exhibiting ease of handling superior to that of a conventional material composed of a substrate layer comprising a water-soluble polymer and a coat layer comprising aliphatic ester, when it is moistened. A material prepared with the use of a biodegradable polymer has also been known. In particular, a material comprising a laminate of a biodegradable polymer and a water-soluble polymer for the purpose of improving ease of handling has also been known. For example, JP 2014-140978 A discloses a laminate of a flexible water-insoluble resin sheet, a thin film of a water-insoluble polymer, and a water-soluble polymer film comprising a water-soluble polymer stacked in that order on top of the other, which can exhibit improved ease of handling when a water-insoluble polymer thin film is applied to a target. WO 2015/194616 discloses a laminate excellent in biocompatibility, easy to handle, and suitable for medical application such as an adhesion prevention film, composed of a fiber structure in which water-soluble resin and a layer comprising polylactic acid resin are stacked on top of each other.

Conventional materials for adhesion prevention have features to be improved in terms of functions as materials for adhesion prevention and ease of handling at the time of use. For example, since the material for adhesion prevention disclosed in WO '162 comprises a substrate layer comprising a water-soluble polymer that is covered by a coat layer comprising aliphatic ester and, in addition, it is difficult to remove the coat layer therefrom, adhesion between the substrate layer and biological tissue is thought to be become insufficient. Concerning the materials disclosed in JP '978 and WO '616, regulation of biodegradability of the biodegradable polymers is not sufficiently examined. Therefore, when such materials are indwelled in the body, accordingly, such materials is thought to be remain in the body for a long period of time. Accordingly, it could be helpful to provide a material for adhesion prevention having a handling property of being able to be adhered to biological tissue with certainty and of which tissue adhesiveness and biodegradability has been improved.

SUMMARY

We discovered a composition of a material for adhesion prevention excellent in terms of strength, ease of handling, and degradability when indwelled in the body. We thus provide:

(1) A material for adhesion prevention composed of a 1 to 1,000 μm-thick water-soluble support layer comprising a water-soluble polymer and a 10 to 1,000 nm-thick adhesion prevention layer comprising a biodegradable polymer, wherein the biodegradable polymer is composed of a branched polyalkylene glycol comprising 3 to 8 terminal hydroxyl groups per molecule bound to a polyhydroxy alkanoic acid and the mass ratio of the branched polyalkylene glycol relative to the total mass is 1% to 40%.

(2) The material for adhesion prevention according to (1), wherein the branched polyalkylene glycol is composed of linear polyalkylene glycol bound to a polyhydric alcohol.

(3) The material for adhesion prevention according to (1) or (2), wherein the polyhydroxy alkanoic acid is a homopolymer of monomers selected from the group consisting of lactic acid, glycolic acid, and caproic acid or a copolymer of two or more of the monomers.

(4) The material for adhesion prevention according to any of (1) to (3), wherein the biodegradable polymer has a structure represented by Formula (I):

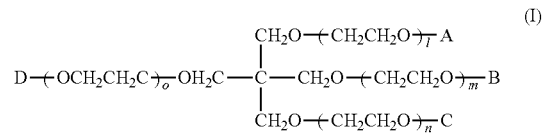

wherein, l, m, n, and o are each independently an integer of 24 to 88 and A, B, C, and D each independently represent a group represented by Formula (II):

wherein, x is an integer of 90 to 148 or a group represented by Formula (III):

wherein, y is an integer of 72 to 132 and z is an integer of 19 to 39.

(5) The material for adhesion prevention according to any of (1) to (4), wherein the biodegradable polymer has a structure represented by Formula (IV):

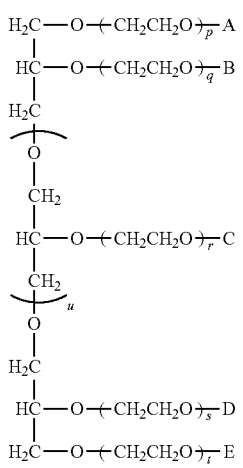

(IV)

wherein, p, q, r, s, and t are each independently in each repeating unit an integer of 5 to 20, u is an integer of 0 to 4, and A, B, C, D, and E each independently in each repeating unit represent a group represented by Formula (II):

(II)

wherein, x is an integer of 40 to 80 or a group represented by Formula (III):

(III)

wherein, y is an integer of 35 to 65 and z is an integer of 9 to 20.

(6) The material for adhesion prevention according to any of (1) to (5), wherein the polyhydroxy alkanoic acid in the biodegradable polymer represented by Formulae (I) and (IV) is a copolymer of lactic acid and glycolic acid and the ratio of the molar number of the lactic acid relative to the molar number of the glycolic acid in the biodegradable polymer is 3.0 to 5.0.

(7) The material for adhesion prevention according to any of (1) to (6), wherein the water-soluble polymer is a polysaccharide or modified polysaccharide.

(8) The material for adhesion prevention according to any of (1) to (6), wherein the water-soluble polymer is selected from the group consisting of pullulan, hyaluronic acid, acylated pullulan, acylated hyaluronic acid, acetylated pullulan, acetylated hyaluronic acid, and a mixture of two or more thereof.

(9) The material for adhesion prevention according to any of (1) to (8), wherein the support layer is provided on a substrate, the support layer is adhered to the substrate with a strength that can be stripped off from the substrate, and the adhesion prevention layer is provided on the support layer.

The material for adhesion prevention has sufficient strength and ease of handling to be adhered to a target site in the body and excellent biodegradability in the body. With the use of the material for adhesion prevention, development of complications caused by adhesion in a post-operative patient can be suppressed in a more efficient manner than conventional materials.

DETAILED DESCRIPTION

Figure 1:
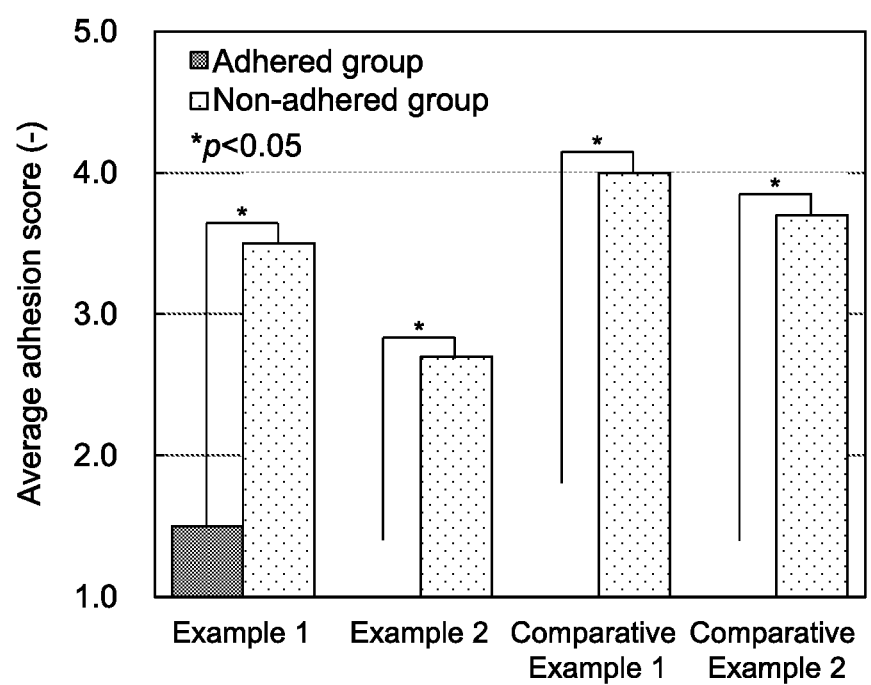
FIG. 1 shows a chart demonstrating the results of evaluation of the materials for adhesion prevention of Examples 1 and 2 and Comparative Examples 1 and 2 concerning the ability for adhesion prevention using mice.

Summary of Composition of Material for Adhesion Prevention

The material for adhesion prevention comprises a water-soluble support layer comprising a water-soluble polymer and an adhesion prevention layer comprising a biodegradable polymer. The support layer may be provided on at least either one of an upper layer or a lower layer of the adhesion prevention layer, or the adhesion prevention layer may be sandwiched by two support layers provided on both of the upper layer and the lower layer. It is preferable that the support layer be adjacent to the adhesion prevention layer. When the adhesion prevention layer is sandwiched by two support layers, at least one support layer is preferably adjacent to the adhesion prevention layer. Alternatively, a layer comprising a drug such as an anti-inflammatory drug may be provided between the support layer and the adhesion prevention layer.

Adhesion Prevention Layer

An adhesion prevention layer is indwelled in the body in the end to exert a function of adhesion prevention. An adhesion prevention layer comprises a biodegradable polymer, and thickness thereof is 10 to 1,000 nm. From the viewpoint of improvement in strength and ease of handling, thickness of the adhesion prevention layer is preferably 25 nm or more, more preferably 50 nm or more, and further preferably 70 nm or more. From the viewpoint of adhesiveness to the body and degradability in the body, thickness is preferably 500 nm or less, more preferably 300 nm or less, and further preferably 200 nm or less. The thickness of the adhesion prevention layer can be measured by, for example, observing a difference in levels between the adhesion prevention layer provided on a silicon wafer and the silicon wafer under an atomic force microscope.

The content of the biodegradable polymer in the adhesion prevention layer is preferably 90% by mass or more, and more preferably 95% by mass or more, relative to the total mass of the adhesion prevention layer. The adhesion prevention layer may consist of the biodegradable polymer alone. However, the adhesion prevention layer may contain various additives, provided that physical properties thereof are not adversely affected. The amount of additives is preferably 0% to 5% by mass relative to the total mass of the adhesion prevention layer. Examples of additives include an antioxidant, a weatherproof stabilizer, a heat stabilizer, a lubricant, a nucleating agent, an ultraviolet absorber, and a colorant. A plurality of types of additives may be contained. In addition to the additives mentioned above, particles of inorganic or organic compounds may be contained. The amount of particles is preferably 0% to 5% by mass relative to the total mass of the adhesion prevention layer. Examples of particles include particles of calcium carbonate, titanium dioxide, silicon dioxide, calcium fluoride, lithium fluoride, alumina, barium sulfate, zirconia, and calcium phosphate, cross-linked polystyrene particles, and metallic nanoparticles.

The adhesion prevention layer preferably becomes a film after the water-soluble support layer is dissolved as described below. The term "film" used herein generally refers to a construct that is two-dimensionally spread, and forms referred to as a sheet and a plate are within the scope of the film. A film may be discontinuous by lacking a part thereof or it may be porous.

The adhesion prevention layer is composed of a material with biocompatibility. A material with "biocompatibility" or "bioaffinity" refers to a substance that imparts no or substantially no stimuli or adverse influence on biological tissue. More specifically, such material does not generate or elute any substance harmful to the biological tissue, and the biological tissue that had been brought into contact with the material does not exhibit protective reactions such as inflammation or blood clotting, against the material by recognizing the material as a foreign body.

Biodegradable Polymer

A biodegradable polymer has a structure in which a branched polyalkylene glycol having 3 to 8 terminal hydroxyl groups per molecule is bound to polyhydroxy alkanoic acid; i.e., a block copolymer structure. When an average molecular weight of the biodegradable polymer is excessively small, intermolecular interactions are attenuated, an ability of film formation is deteriorated, and strength of the resulting film is not sufficient. When an average molecular weight is excessively large, in contrast, the viscosity is increased when the polymer is dissolved in a solvent, and film formation process becomes difficult.

Polyhydroxy alkanoic acid may be a homopolymer comprising one type of monomers or a copolymer comprising two or more types of monomers. When polyhydroxy alkanoic acid is a copolymer, it may be a random or block copolymer. Specific examples of monomers constituting polyhydroxy alkanoic acid include lactic acid, 3-hydroxybutyric acid, glycolic acid, and caproic acid. A specific example of a starting monomer generating polyhydroxy alkanoic acid is ε-caprolactone. Polyhydroxy alkanoic acid is preferably a homopolymer of monomers selected from the group consisting of lactic acid, glycolic acid, and caproic acid or a copolymer comprising two or more of the monomers mentioned above. From the viewpoint of sufficient biodegradability, polyhydroxy alkanoic acid is preferably a copolymer, and particularly preferably a random copolymer, of lactic acid and glycolic acid. In such an example, the ratio of the molar number of the lactic acid is preferably 3.0 to 5.0 relative to the molar number (1.0) of the glycolic acid in the copolymer. A monomer constituting polyhydroxy alkanoic acid may be of either an L form or D form. A D form and an L form may be simultaneously present in a polymer according to need (a DL form). From the viewpoint of good physical properties such as mechanical strength, a polymer is preferably of either the D form or L form.

It is preferable that a branched polyalkylene glycol has a structure in which polyalkylene glycol is bound to at least some and preferably all of a plurality of hydroxyl groups of a polyhydric alcohol. However, the structure is not limited thereto, and polyalkylene glycol may not bind to some hydroxyl groups of the polyhydric alcohol. It is preferable that the branched polyalkylene glycol has a structure in which linear polyalkylene glycol is bound to a polyhydric alcohol so that mechanical strength is enhanced. A polyhydric alcohol preferably comprises 3 or more, and more preferably 4 or more hydroxyl groups. Specific examples of a polyhydric alcohol include glycerin, polyglycerin (in particular, a dimer to a hexamer of glycerin), pentaerythritol, and saccharides such as glucose, fructose, xylose, galactose, mannose, erythrose, arabinose, sucrose, maltose, lactose, trehalose, and cellobiose. Since such polyhydric alcohols have biocompatibility, they are particularly preferable as starting materials of materials for adhesion prevention.

When the number of polyalkylene glycol chains bound to the hydroxyl group of the polyhydric alcohol is excessively small, intermolecular interactions are attenuated. When the number thereof is excessively large, in contrast, steric hindrance occurs, and reactivity in the polymerization reaction of hydroxyalkanoic acid to the terminal hydroxyl group may be deteriorated, or the ability of film formation or mechanical properties of the biodegradable polymer may be deteriorated. Accordingly, the number of polyalkylene glycol chains binding to a molecule of a polyhydric alcohol is preferably 3 to 8, more preferably 3 to 6, further preferably 3 to 5, and particularly preferably 3 to 4.

The mass ratio of the branched polyalkylene glycol relative to the total mass of the biodegradable polymer is 1% to 40%. When the content of branched polyalkylene glycol is excessively low, flexibility of the film becomes insufficient, and it becomes difficult to fit the shape of the biological tissue. When the content is excessively large, in contrast, the ability of film formation is deteriorated, water solubility becomes excessively high, and the film is disadvantageously dissolved immediately after it is applied to the biological tissue. Thus, the mass ratio of the branched polyalkylene glycol block relative to the total mass of the block copolymer is preferably 1% or more, more preferably 5% to 40%, and particularly preferably 25% or less, such as 5% to 40%.

The mass ratio and the number average molecular weight of each block relative to the total mass of the block copolymer comprising the polyhydroxy alkanoic acid block and the polyalkylene glycol block can be determined by subjecting the block copolymer to $^1$H-NMR assays based on the integral value of proton chemical shift signals derived from chemical structures characteristic to the polyhydroxy alkanoic acid and the polyalkylene glycol, respectively, and the number of hydrogen atoms in the repeating unit and the number average molecular weight of the repeated monomers.

In a block copolymer comprising a branched polyethylene glycol block and a poly(lactic acid-glycolic acid) copolymer, for example, a relative integral value of signals derived from 4 hydrogen atoms of an ethylene group of polyethylene glycol exhibiting a chemical shift of 3.4 to 3.7 ppm is designated as A, a relative integral value of signals derived from 3 hydrogen atoms of a methyl group of lactic acid exhibiting a chemical shift of 1.4 to 1.6 ppm is designated as B, and a relative integral value of signals derived from 2 hydrogen atoms of a methylene group of glycolic acid exhibiting a chemical shift of 4.7 to 4.9 ppm is designated as C. In such an example, the mass ratio of branched polyethylene glycol and polyhydroxy alkanoic acid relative to the total mass of the block copolymer is represented by Equations (1) and (2) with the use of the molecular weights of the repeated monomer units of 44, 72, and 58, respectively. Also, the number average molecular weight of branched polyethylene glycol and that of polyalkanoic acid can be determined by multiplying the number average molecular weight of the block copolymer by the mass ratio of each block.

$$\text{Mass ratio of branched polyethylene glycol (\%)} = 100 \times (44 \times A/4)/((44 \times A/4) + (72 \times B/3) + (58 \times C/2)) \quad (1)$$

$$\text{Mass ratio of polyhydroxy alkanoic acid (\%)} = 100 \times ((72 \times B/3) + (58 \times C/2))/((44 \times A/4) + (72 \times B/3) + (58 \times C/2)) \quad (2)$$

The ratio of the molar number of each of the constitutive monomers in the polyhydroxy alkanoic acid block in the copolymer can be determined by subjecting the block copolymer to $^1$H-NMR assays based on the integral value of proton chemical shift signals derived from chemical structures characteristic of the polyhydroxy alkanoic acid and polyalkylene glycol, respectively, and the number of hydrogen atoms in the repeating unit and the number average molecular weight of the repeated monomers.

When the polyhydroxy alkanoic acid block in the copolymer is a copolymer of lactic acid and glycolic acid, for example, the ratio of the molar number of the lactic acid relative to the molar number of the glycolic acid is represented by Equation (3) with the use of the relative integral value B of signals derived from 3 hydrogen atoms of the methyl group of lactic acid exhibiting a chemical shift of 1.4 to 1.6 ppm and a relative integral value C of signals derived from 2 hydrogen atoms exhibiting a chemical shift of 4.7 to 4.9 ppm of the methyl group of glycolic acid as used in Equations (1) and (2).

Ratio of molar number of lactic acid relative to molar number of glycolic acid in copolymer=
(B/3)/(C/2)  (3)

As branched polyalkylene glycol, specifically, the "SUNBRIGHT® PTE" series commercially available from NOF Corporation, which has a structure in which a polyethylene glycol chain is bound to the hydroxyl group of pentaerythritol, and "SUNBRIGHT® HGEO" series, which has a structure in which polyethylene glycol is bound to a hydroxyl group of polyglycerin having 8 hydroxyl groups, can be preferably used.

According to a preferred example, the biodegradable polymer has a structure represented by Formula (I):

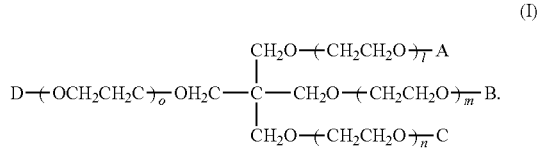

In Formula (I), l, m, n and o are each independently an integer of 24 to 88 and A, B, C, and D each independently represent a group represented by Formula (II):

wherein, x is an integer of 90 to 148 or a group represented by Formula (III):

wherein, y is an integer of 72 to 132 and z is an integer of 19 to 39. In Formula (III), a component within square brackets indicates that a monomer unit in parentheses is randomly polymerized (the same applies hereinbelow).

According to another preferred example, the biodegradable polymer has a structure represented by Formula (IV):

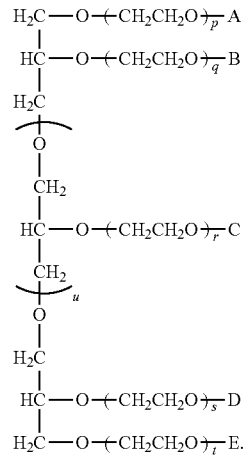

In Formula (IV), p, q, r, s, and t are each independently in each repeating unit an integer of 5 to 20, u is an integer of 0 to 4, and A, B, C, D, and E each independently in each repeating unit represent a group represented by Formula (II):

wherein, x is an integer of 40 to 80 or a group represented by Formula (III):

wherein, y is an integer of 35 to 65 and z is an integer of 9 to 20.

Method of Producing Biodegradable Polymer

A branched polyalkylene glycol can be bound to a polyhydroxy alkanoic acid by any method. Examples of methods include a method in which polymerization of hydroxyalkanoic acid is initiated from the terminal hydroxyl group of the polyalkylene glycol chain and a method in which a branched polyalkylene glycol is bound to polyhydroxy alkanoic acid via condensation. More specifically, a biodegradable polymer can be obtained by, for example, in the presence of a branched polyalkylene glycol, subjecting a cyclic ester intermediate of hydroxyalkanoic acid such as lactide to ring-opening polymerization with the use of a catalyst such as tin octoate under a reduced pressure. Conventional methods of producing polyhydroxy alkanoic acid can be employed in a method of removing moisture or a low-molecular-weight compound by adjusting conditions in heat reflux in an organic solvent for polymerization or a method of suppressing a depolymerization reaction by inactivating a catalyst after the completion of the polymerization reaction. For example, the resulting block copolymer is thermally treated under a reduced pressure, and an unreacted cyclic ester intermediate can be sublimated and removed.

Biodegradability of Adhesion Prevention Layer

Concerning the material for adhesion prevention, an adhesion prevention layer that is indwelled in the body and exerts functions of adhesion prevention is excellent in biodegradability, in particular. Biodegradability is a concept that encompasses both hydrolysis and enzymolysis caused by an enzyme present in the body.

When a polymer with biocompatibility is indwelled over a period of several months to several years, it is highly likely that, for example, inflammation caused by a foreign body reaction occurs. Accordingly, an adhesion prevention layer indwelled in the body preferably has biodegradability such that the mass thereof would be approximately halved from the initial level over a period of approximately 28 days after the initiation of retention. Accordingly, biodegradability of the adhesion prevention layer can be characterized in that a percentage of the mass decreased 28 days after the initiation of treatment is preferably 50% or more, 55% or more, and 60% or more, relative to the mass before soaking when 1 mg of the sample is soaked in 10 ml of phosphate buffered saline (PBS) at 37° C. and continuously and mildly shaken at approximately 50 rpm. The percentage of the mass decreased 28 days after the initiation of treatment is more preferably 70% or more, further preferably 95% or more, and particularly preferably 100%.

Support Layer

A support layer comprises a water-soluble polymer, and thickness thereof is 1 to 1,000 µm. A support layer is capable of retaining a shape of a material for adhesion prevention when transferred to the target biological tissue, it can be dissolved upon moistening when applied to the biological tissue, and it can be removed without stripping or other procedures. The thickness of a support layer is preferably 10 µm or more from the viewpoint of an improvement in strength and ease of handling of the material for adhesion prevention. Thickness is preferably 500 µm or less, and more preferably 300 µm or less, to adequately reduce the time until the material is dissolved in water. For example, thickness of a support layer is further preferably 10 to 300 µm. The thickness of a support layer can be determined by, for example, using a 0.001 mm or 0.01 mm dial thickness gauge, measuring thickness at arbitrary 10 points, and determining the average thereof.

The support layer preferably comprises a water-soluble polymer in an amount of 90% by mass or more, and particularly preferably 95% by mass or more. The support layer may consist of a water-soluble polymer. The water-soluble polymer preferably has biocompatibility to prevent an aqueous solution thereof from causing inflammation in the body. Examples of water-soluble polymers having biocompatibility include a polysaccharide, a modified polysaccharide, a protein, and other water-soluble synthetic polymers. Specific examples thereof include pullulan, hyaluronic acid, alginic acid, hydroxypropylcellulose, hydroxypropyl methylcellulose, carboxymethyl cellulose, acylated pullulan, acylated hyaluronic acid, acetylated pullulan, acetylated hyaluronic acid, polyvinyl alcohol, polyvinyl acetal, polyvinyl formal, polyacrylic acid, polymethacrylic acid, polyethylene glycol, polyacrylamide, guar gum, Locust bean gum, pregelatinized starch, polyvinyl pyrrolidone, a polyvinyl pyrrolidone-vinyl acetate block copolymer, and a salt of any thereof. Among them, pullulan, hyaluronic acid, acylated pullulan, acylated hyaluronic acid, acetylated pullulan, and acetylated hyaluronic acid that are particularly excellent in biocompatibility are preferable, and pullulan and hyaluronic acid are more preferable, as water-soluble polymers.

The time until the support layer is dissolved in water upon contact therewith is preferably at least 10 seconds, more preferably at least 15 seconds, and further preferably at least 30 seconds because of ease of handling since the material for adhesion prevention can be reapplied to the biological tissue. The time until the support layer is dissolved is preferably 5 minutes or shorter, more preferably 3 minutes or shorter, and further preferably 2 minutes or shorter so that the support layer can be removed immediately after it is applied to the biological tissue and the duration of treatment can be shortened. The time until the support layer is dissolved in water upon contact therewith is a time during which a drop of water (about 0.04 ml) is transferred from the water-soluble support layer to the other surface. When water reaches the other surface, the support layer is gradually dissolved from the surface from which water is applied dropwise to the support layer, the shape of the other surface cannot be retained, and the support layer is thus dissolved.

The support layer may be composed of a homogeneous single layer or a plurality of layers. As long as the support layer comprises a water-soluble polymer and has sufficient water solubility, a configuration of the support layer may be any of, for example, a film, an unwoven fabric, a mesh, or a hydrogel. When the support layer is composed of a plurality of layers, thickness of each layer is not particularly limited, provided that the thickness of the whole support layer is within the range described above. For example, thickness of each layer can be at least 0.1 µm, and preferably 1 µm to 800 µm, and particularly preferably 500 µm.

Substrate

The material for adhesion prevention may comprise a support layer supported by a substrate. In such an example, preferably, the support layer is adhered to the substrate with a strength that can be stripped off from the substrate while the adhesion prevention layer is integrally adhered to the support layer with a strength that cannot be stripped off from the support layer. Thus, the material for adhesion prevention can be handled while supporting a laminate of the support layer and the adhesion prevention layer on the substrate up to immediately before application thereof to the biological tissue, and the laminate of the support layer and the adhesion prevention layer can be stripped off from the substrate at the time of application. Such a configuration is preferable because of further improved ease of handling.

A material constituting the substrate is not particularly limited, and a substrate composed of an arbitrary material such as a glass substrate, a metal substrate, or a resin substrate, can be used. From the viewpoint of economic efficiency and surface smoothness, however, use of a resin substrate such as a plastic film is preferable. A flexible substrate is more preferable from the viewpoint of improved ease of handling. A substrate is preferably a film comprising polyester such as polyethylene terephthalate (PET) or polybutylene terephthalate (PBT). In addition, thickness is preferably 0.1 to 300 µm from the viewpoint of flexibility.

Method of Producing Material for Adhesion Prevention

The material for adhesion prevention can be produced by, for example, coating the substrate with a solution containing a water-soluble polymer to form a support layer, and coating the support layer with a solution containing a biodegradable polymer to form an adhesion prevention layer. We also provide a method of producing a material for adhesion prevention comprising a step of coating a substrate with a solution containing a water-soluble polymer to form a support layer and a step of coating the support layer with a solution containing a biodegradable polymer to form an adhesion prevention layer. Any solvent can be used to dissolve a polymer. In a water-soluble polymer, a water-miscible organic solvent such as water or ethanol can be preferably used. In a biodegradable polymer, a polar organic solvent such as ethyl acetate, acetone, or dichloromethane can be preferably used.

A method of coating of a polymer-containing solution is not particularly limited. For example, a conventional technique such as spin coating, gravure coating, direct lip coating, slot coating, comma coating, inkjet printing, or silk screen printing can be employed. As described above, a substrate of an arbitrary material can be used. According to need, a substrate may be subjected to, for example, treatment of adhesion promotion such as corona discharge treatment in the air, a nitrogen gas, or a gas mixture of nitrogen and carbon dioxide or under other atmospheres, plasma treatment under a reduced pressure, flame treatment, or ultraviolet treatment before coating of a polymer-containing solution. Alternatively, the substrate may be subjected to anchor treatment using an anchoring agent such as urethane resin, epoxy resin, or polyethyleneimine.

Method of Using Material for Adhesion Prevention

Our method for adhesion prevention comprises adhering the material for adhesion prevention to biological tissue. This method comprises: in the presence of a substrate, a step of removing a laminate comprising a support layer and an adhesion prevention layer from the substrate; a step of bringing the laminate into contact with an area in which biological tissue adhesion should be prevented to adhere the laminate thereto; and a step of moistening the laminate to dissolve the support layer. The laminate may be adhered to biological tissue in a manner such that either the support layer or the adhesion prevention layer would be brought into contact with the biological tissue. It is preferable that the adhesion prevention layer be brought into direct contact with biological tissue so that the adhesion prevention layer would be adhered to biological tissue with higher certainty. When the laminate adhered to biological tissue is moistened by, for example, applying water thereto, the support layer is dissolved immediately, and the adhesion prevention layer is selectively indwelled in biological tissue. The indwelled adhesion prevention layer exerts functions of adhesion prevention in biological tissue. The method involving the use of the material for adhesion prevention enables application of a material for adhesion prevention comprising a polymer that is excellent in terms of biodegradability, thickness to fit the shape of biological tissue and adhesiveness thereto, and a low level of stress imposed on the body. Thus, development of complications caused by post-operational adhesion can be suppressed.

EXAMPLES

Hereafter, our materials and methods are described in greater detail with reference to the examples, although this disclosure is not limited to these examples.

1. Production of Material for Adhesion Prevention

Example 1

L-lactide (PURASORB® L, manufactured by Corbion) was subjected to polymerization with each terminal hydroxyl group of the 4-arm-branched polyethylene glycol derivative (pentaerythritol polyethylene glycol, SUNBRIGHT® PTE-10T, manufactured by NOF Corporation) (hereafter, this 4-arm-branched polyethylene glycol derivative is referred to as "4 PEG") to synthesize a 4 PEG-PLLA block copolymer with the number average molecular weight of approximately 40,000 determined by $^1$H-NMR (apparatus: EX-270; frequency: 400 MHz; solvent: deuterochloroform; number of integration: 8; temperature: room temperature (about 25° C.)) based on the assumption that the molecular weight of PTE-10T was 10,000. The obtained 4 PEG-PLLA has a structure represented by Formulae (I) and (II).

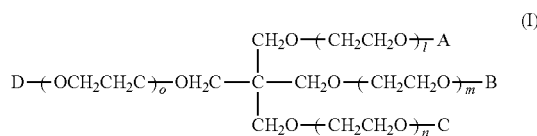

In Formula (I), l, m, n, and o are each independently an integer of 50 to 60 and A, B, C, and D each independently represent a group represented by Formula (II).

In Formula (II), x is an integer of 100 to 125.

An aqueous solution of pullulan (pullulan in the Japanese Pharmacopoeia, manufactured by Hayashibara Co., Ltd.) with the weight average molecular weight of approximately 200,000 (an aqueous solution with solid content of 10% by mass; viscosity at 30° C.; 100 to 180 mm$^2$/sec) was applied on a biaxially stretched polyester (PET) film (Lumirror® type: T60; thickness: 100 manufactured by Toray industries, Inc.) (hereafter, this film is referred to as a "PET substrate") via gravure coating to provide a 10-μm-thick water-soluble support layer. The thickness of the support layer was determined by using a dial thickness gauge (SM-1201L; manufactured by Teclock; dial: 0.001 mm; measuring force: 1.5 N or lower), measuring thickness at arbitrary 10 points, determining the average thereof, and subtracting the thickness of the PET substrate from the average.

Subsequently, the water-soluble support layer prepared in the manner described above was coated with a solution of the 4 PEG-PLLA block copolymer dissolved in ethyl acetate heated to 70° C. via gravure coating to provide a 120 nm-thick adhesion prevention layer.

The thickness of the adhesion prevention layer was measured in the manner described below. The test piece obtained from the material for adhesion prevention was soaked in water to dissolve the water-soluble support layer, the stripped adhesion prevention layer was mounted on a 40 mm×40 mm silicon wafer (P type silicon wafer; manufactured by KST World Corp.; diameter: 100±0.5 mm; total thickness: 525±25 μm; oxide film thickness: 200 nm; crystal plane indices: 100; soaked in a solution containing sulfuric acid and hydrogen peroxide at 3:1 by volume for 10 minutes before use and washed with deionized water (resistance: 18 Ωcm)), the resultant was thoroughly dried, a region of 100 μm×25 μm was scanned using an atomic force microscope (nanoscale hybrid microscope VN-8000 (tapping mode); manufactured by Keyence Corporation), and a difference in levels between the silicon wafer and the adhesion prevention layer was measured as film thickness.

Example 2

L-lactide (PURASORB® L, manufactured by Corbion) and glycolide (PURASORB® G, manufactured by Corbion) were subjected to random polymerization with each terminal hydroxyl group of 4 PEG (SUNBRIGHT® PTE-10T, manufactured by NOF Corporation) to synthesize a 4 PEG-PLGA block copolymer with the number average molecular weight of approximately 46,000 determined by performed under the same conditions as in Example 1 based on the assumption that the molecular weight of PTE-10T was 10,000. The ratio of the molar number of lactic acid relative to the molar number (1.0) of glycolic acid was 4.1. The resulting 4 PEG-PLGA block copolymer has a structure represented by Formulae (I) and (III).

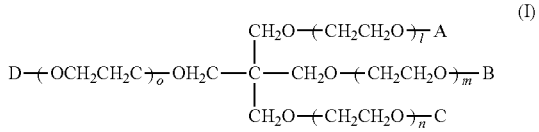  (I)

In Formula (I), l, m, n, and o are each independently an integer of 50 to 60 and A, B, C, and D each independently represent a group represented by Formula (III).

  (III)

In Formula (III), y is an integer of 90 to 120 and z is an integer of 23 to 33.

A water-soluble support layer was provided on a PET substrate in the same manner as in Example 1, and a solution prepared by dissolving the 4 PEG-PLGA block copolymer obtained above in ethyl acetate heated to 55° C. was applied thereon via gravure coating to provide a 150-nm-thick adhesion prevention layer. The thickness of the adhesion prevention layer was measured in the same manner as in Example 1.

Example 3

L-lactide (PURASORB® L, manufactured by Corbion) was subjected to polymerization with each terminal hydroxyl group of the 8-arm-branched polyethylene glycol derivative (SUNBRIGHT® HGEO-50H, manufactured by NOF Corporation) (hereafter, the 8-arm-branched polyethylene glycol derivative is referred to as "8 PEG") to synthesize a 8 PEG-PLLA block copolymer with the number average molecular weight of approximately 43,000 determined by $^1$H-NMR performed under the same conditions as in Example 1 based on the assumption that the molecular weight of HGEO-50H was 5,000. The resulting 8 PEG-PLLA block copolymer has a structure represented by Formulae (IV) and (II).

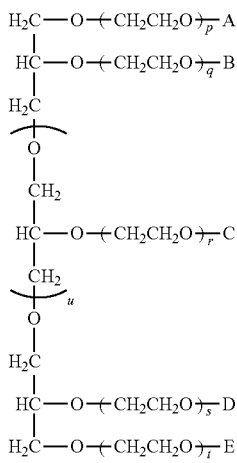  (IV)

In Formula (IV), p, q, r, s, and t are each independently an integer of 10 to 15, u is 4, and A, B, C, D, and E each independently in each repeating unit represent a group represented by Formula (II).

  (II)

In Formula (II), x is an integer of 50 to 70.

A water-soluble support layer was provided on a PET substrate in the same manner as in Example 1, and a solution prepared by dissolving the 8 PEG-PLLA block copolymer obtained above in dichloromethane at room temperature was applied thereon via gravure coating to provide a 150-nm-thick adhesion prevention layer. The thickness of the adhesion prevention layer was measured in the same manner as in Example 1.

Example 4

With the use of pullulan and the PET substrate as used in Example 1, the 5-µm-thick first water-soluble support layer was provided on the PET substrate via gravure coating. The thickness of the support layer was measured in the same manner as in Example 1.

On the first water-soluble support layer provided in the manner described above, subsequently, a solution prepared by dissolving the 4 PEG-PLGA block copolymer obtained in Example 2 in ethyl acetate heated to 55° C. was applied thereon via gravure coating to provide a 150-nm-thick adhesion prevention layer. The thickness of the adhesion prevention layer was measured in the same manner as in Example 1.

At the outset, another PET substrate was prepared separately from the PET substrate on which the adhesion prevention layer and the first water-soluble support layer had been provided. With the use of pullulan and the PET substrate as used in Example 1, the 300-µm-thick second water-soluble support layer of an unwoven fabric with the weight per unit area of 50 g/m$^2$ was provided on the PET substrate via dry spinning. The thickness of the second water-soluble support layer was measured in the same manner as in Example 1, and the weight per unit area was measured by the method described in JIS L 1096 8.3.2 (1999).

The first water-soluble support layer and the adhesion prevention layer were stripped off from the PET substrate. Pure water was sprayed on the first water-soluble support layer in an amount of 5 g/m$^2$ with the use of an accumulator sprayer (manufactured by Maruhachi Industrials). Immediately thereafter, the stripped adhesion prevention layer was adhered to the second water-soluble support layer.

Example 5

In the same manner as in Example 4, the 4 PEG-PLGA block copolymer obtained in Example 2 was provided as the adhesion prevention layer to a thickness of 150 nm on the 5-µm-thick water-soluble support layer of pullulan provided on the PET substrate. The thickness of each layer was measured in the same manner as in Example 1.

In the same manner as in Example 4, the 800-µm-thick second water-soluble support layer of an unwoven fabric with the weight per unit area of 160 g/m$^2$ was provided on a PET substrate via dry spinning. The thickness and the weight per unit are of the second water-soluble support layer were measured in the same manner as in Example 4.

In the same manner as in Example 4, the first water-soluble support layer and the adhesion prevention layer were stripped off from the PET substrate. Pure water was sprayed on the first water-soluble support layer in an amount of 5 g/m$^2$ with the use of an accumulator sprayer. Immediately thereafter, the stripped adhesion prevention layer was adhered to the second water-soluble support layer.

Example 6

In the same manner as in Example 2, L-lactide (PURASORB® L, manufactured by Corbion) and glycolide (PURASORB® G, manufactured by Corbion) were subjected to random polymerization with each terminal hydroxyl group of 4 PEG (SUNBRIGHT® PTE-10T, manufactured by NOF Corporation) to synthesize a 4 PEG-PLGA block copolymer with the number average molecular weight of approximately 30,000 determined by $^1$H-NMR performed under the same conditions as in Example 1 based on the assumption that the molecular weight of PTE-10T was 10,000. The ratio of the molar number of lactic acid relative to the molar number (1.0) of glycolic acid was 4.2. The resulting 4 PEG-PLGA block copolymer has a structure represented by Formulae (I) and (III).

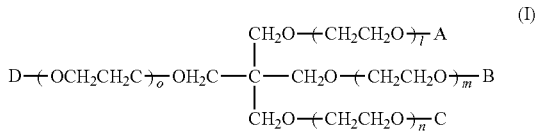

In Formula (I), l, m, n, and o are each independently an integer of 50 to 60 and A, B, C, and D each independently represent a group represented by Formula (III).

In Formula (III), y is an integer of 40 to 80 and z is an integer of 9 to 20.

In the same manner as in Example 4, a 5-μm-thick water-soluble support layer of pullulan was provided on the PET substrate, and a solution prepared by dissolving the 4 PEG-PLGA block copolymer obtained above in ethyl propionate heated to 60° C. was applied on the PET substrate via gravure coating to provide a 150-nm-thick adhesion prevention layer. The thickness of each layer was measured in the same manner as in Example 1.

In the same manner as in Example 4, the 300-μm-thick second water-soluble support layer of an unwoven fabric with the weight per unit area of 160 g/m$^2$ was provided on a PET substrate via dry spinning. The thickness and the weight per unit are of the second water-soluble support layer were measured in the same manner as in Example 4.

In the same manner as in Example 4, the first water-soluble support layer and the adhesion prevention layer were stripped off from the PET substrate. Pure water was sprayed on the first water-soluble support layer in an amount of 5 g/m$^2$ with the use of an accumulator sprayer. Immediately thereafter, the stripped adhesion prevention layer was adhered to the second water-soluble support layer.

Example 7

In the same manner as in Example 2, L-lactide (PURASORB® L, manufactured by Corbion) and glycolide (PURASORB® G, manufactured by Corbion) were subjected to random polymerization with each terminal hydroxyl group of 4 PEG (SUNBRIGHT® PTE-10T, manufactured by NOF Corporation) to synthesize a 4 PEG-PLGA block copolymer with the number average molecular weight of approximately 40,000 determined by $^1$H-NMR performed under the same conditions as in Example 1 based on the assumption that the molecular weight of PTE-10T was 10,000. The ratio of the molar number of lactic acid relative to the molar number (1.0) of glycolic acid was 4.0. The resulting 4 PEG-PLGA block copolymer has a structure represented by Formulae (I) and (III).

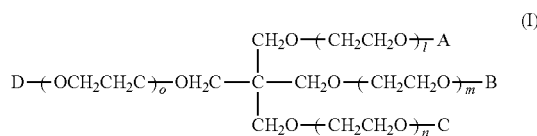

In Formula (I), l, m, n, and o are each independently an integer of 50 to 60 and A, B, C, and D each independently represent a group represented by Formula (III).

In Formula (III), y is an integer of 70 to 110 and z is an integer of 16 to 28.

In the same manner as in Example 4, a 5-μm-thick water-soluble support layer of pullulan was provided on the PET substrate, and a solution prepared by dissolving the 4 PEG-PLGA block copolymer obtained above in ethyl propionate heated to 60° C. was applied thereon via gravure coating to provide a 150-nm-thick adhesion prevention layer. The thickness of each layer was measured in the same manner as in Example 1.

In the same manner as in Example 4, the 300-μm-thick second water-soluble support layer of an unwoven fabric with the weight per unit area of 160 g/m$^2$ was provided on a PET substrate via dry spinning. The thickness and the weight per unit are of the second water-soluble support layer were measured in the same manner as in Example 4.

In the same manner as in Example 4, the first water-soluble support layer and the adhesion prevention layer were stripped off from the PET substrate. Pure water was sprayed on the first water-soluble support layer in an amount of 5 g/m$^2$ with the use of an accumulator sprayer. Immediately thereafter, the stripped adhesion prevention layer was adhered to the second water-soluble support layer.

Example 8

In the same manner as in Example 2, L-lactide (PURASORB® L, manufactured by Corbion) and glycolide (PURASORB® G, manufactured by Corbion) were subjected to random polymerization with each terminal hydroxyl group of 4 PEG (SUNBRIGHT® PTE-10T, manufactured by NOF Corporation) to synthesize a 4 PEG-PLGA block copolymer with the number average molecular weight of approximately 60,000 determined by $^1$H-NMR performed under the same conditions as in Example 1 based on the assumption that the molecular weight of PTE-10T was 10,000. The ratio of the molar number of lactic acid relative to the molar number (1.0) of glycolic acid was 4.0. The resulting 4 PEG-PLGA block copolymer has a structure represented by Formulae (I) and (III).

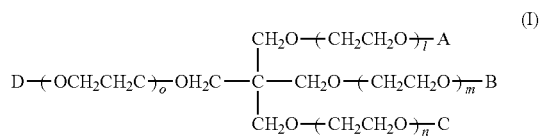

In Formula (I), l, m, n, and o are each independently an integer of 50 to 60 and A, B, C, and D each independently represent a group represented by Formula (III).

In Formula (III), y is an integer of 130 to 160 and z is an integer of 32 to 40.

In the same manner as in Example 4, a 5-μm-thick water-soluble support layer of pullulan was provided on the PET substrate, and a solution prepared by dissolving the 4 PEG-PLGA block copolymer obtained above in ethyl propionate heated to 60° C. was applied thereon via gravure coating to provide a 150-nm-thick adhesion prevention layer. The thickness of each layer was measured in the same manner as in Example 1.

In the same manner as in Example 4, the 300-μm-thick second water-soluble support layer of an unwoven fabric with the weight per unit area of 160 g/m² was provided on a PET substrate via dry spinning. The thickness and the weight per unit are of the second water-soluble support layer were measured in the same manner as in Example 4.

In the same manner as in Example 4, the first water-soluble support layer and the adhesion prevention layer were stripped off from the PET substrate. Pure water was sprayed on the first water-soluble support layer in an amount of 5 g/m² with the use of an accumulator sprayer. Immediately thereafter, the stripped adhesion prevention layer was adhered to the second water-soluble support layer.

Example 9

In the same manner as in Example 2, L-lactide (PURASORB® L, manufactured by Corbion) and glycolide (PURASORB® G, manufactured by Corbion) were subjected to random polymerization with each terminal hydroxyl group of 4 PEG (SUNBRIGHT® PTE-10T, manufactured by NOF Corporation) to synthesize a 4 PEG-PLGA block copolymer with the number average molecular weight of approximately 46,000 determined by $^1$H-NMR performed under the same conditions as in Example 1 based on the assumption that the molecular weight of PTE-10T was 10,000. The ratio of the molar number of lactic acid relative to the molar number (1.0) of glycolic acid was 4.5. The resulting 4 PEG-PLGA block copolymer has a structure represented by Formulae (I) and (III).

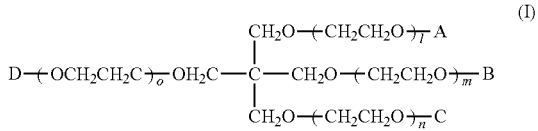

In Formula (I), l, m, n, and o are each independently an integer of 50 to 60 and A, B, C, and D each independently represent a group represented by Formula (III).

In Formula (III), y is an integer of 90 to 125 and z is an integer of 20 to 30.

In the same manner as in Example 4, a 5-μm-thick water-soluble support layer of pullulan was provided on the PET substrate, and a solution prepared by dissolving the 4 PEG-PLGA block copolymer obtained above in ethyl propionate heated to 60° C. was applied thereon via gravure coating to provide a 150-nm-thick adhesion prevention layer. The thickness of each layer was measured in the same manner as in Example 1.

In the same manner as in Example 4, the 300-μm-thick second water-soluble support layer of an unwoven fabric with the weight per unit area of 160 g/m² was provided on a PET substrate via dry spinning. The thickness and the weight per unit are of the second water-soluble support layer were measured in the same manner as in Example 4.

In the same manner as in Example 4, the first water-soluble support layer and the adhesion prevention layer were stripped off from the PET substrate. Pure water was sprayed on the first water-soluble support layer in an amount of 5 g/m² with the use of an accumulator sprayer. Immediately thereafter, the stripped adhesion prevention layer was adhered to the second water-soluble support layer.

Example 10

In the same manner as in Example 2, L-lactide (PURASORB® L, manufactured by Corbion) and glycolide (PURASORB® G, manufactured by Corbion) were subjected to random polymerization with each terminal hydroxyl group of 4 PEG (SUNBRIGHT® PTE-10T, manufactured by NOF Corporation) to synthesize a 4 PEG-PLGA block copolymer with the number average molecular weight of approximately 46,000 determined by performed under the same conditions as in Example 1 based on the assumption that the molecular weight of PTE-10T was 10,000. The ratio of the molar number of lactic acid relative to the molar number (1.0) of glycolic acid was 3.7. The resulting 4 PEG-PLGA block copolymer has a structure represented by Formulae (I) and (III).

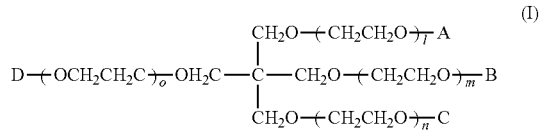

In Formula (I), l, m, n, and o are each independently an integer of 50 to 60 and A, B, C, and D each independently represent a group represented by Formula (III).

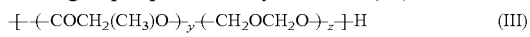

In Formula (III), y is an integer of 88 to 118 and z is an integer of 24 to 32.

In the same manner as in example 4, a 5-μm-thick water-soluble support layer of pullulan was provided on the PET substrate, a solution prepared by dissolving the 4 PEG-PLGA block copolymer obtained above in acetonitrile at room temperature was applied thereon via gravure coating to provide a 150-nm-thick adhesion prevention layer. The thickness of each layer was measured in the same manner as in Example 1.

In the same manner as in Example 4, the 300-μm-thick second water-soluble support layer of an unwoven fabric with the weight per unit area of 160 g/m2 was provided on a PET substrate via dry spinning. The thickness and the weight per unit are of the second water-soluble support layer were measured in the same manner as in Example 4.

In the same manner as in Example 4, the first water-soluble support layer and the adhesion prevention layer were stripped off from the PET substrate. Pure water was sprayed on the first water-soluble support layer in an amount of 5 g/m2 with the use of an accumulator sprayer. Immediately thereafter, the stripped adhesion prevention layer was adhered to the second water-soluble support layer.

Comparative Example 1

A water-soluble support layer was provided on a PET substrate in the same manner as in Example 1, and a solution prepared by dissolving polylactic acid (PURASORB® PDL20, manufactured by Corbion) in ethyl acetate at room temperature was applied thereon via gravure coating to provide a 150-nm-thick adhesion prevention layer. The thickness of the adhesion prevention layer was measured in the same manner as in Example 1.

Comparative Example 2

A water-soluble support layer was provided on a PET substrate in the same manner as in Example 1, and a solution prepared by dissolving a polylactic acid-glycolic acid random copolymer (PURASORB® PDLG5010, manufactured by Corbion) in ethyl acetate heated to 55° C. was applied thereon via gravure coating to provide a 300-nm-thick adhesion prevention layer. The thickness of the adhesion prevention layer was measured in the same manner as in Example 1.

Comparative Example 3

L-lactide (PURASORB® L, manufactured by Corbion) was subjected to polymerization with a hydroxyl group of linear polyethylene glycol (SUNBRIGHT® MEK-20T, manufactured by NOF Corporation) comprising a methyl group at one end and a hydroxyl group at the other end to synthesize a PEG-PLLA block copolymer with the number average molecular weight of approximately 40,000 determined by $^1$H-NMR performed under the same conditions as in Example 1 based on the assumption that the molecular weight of MEK-20T was 20,000. The resulting PEG-PLLA block copolymer has a structure represented by Formula (V).

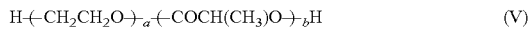

(V)

In Formula (V), a is an integer of 200 to 250 and b is an integer of 260 to 310.

A water-soluble support layer was provided on a PET substrate in the same manner as in Example 1, and a solution prepared by dissolving the PEG-PLLA block copolymer obtained above in dichloromethane at room temperature was applied thereon via gravure coating to provide a 150-nm-thick adhesion prevention layer. The thickness of the adhesion prevention layer was measured in the same manner as in Example 1.

Comparative Example 4

L-lactide (PURASORB® L, manufactured by Corbion) and glycolide (PURASORB® G, manufactured by Corbion) were subjected to random polymerization with a hydroxyl group of linear polyethylene glycol (SUNBRIGHT® MEK-20T, manufactured by NOF Corporation) comprising a methyl group at one end and a hydroxyl group at the other end to synthesize a PEG-PLGA block copolymer with the number average molecular weight of approximately 40,000 determined by $^1$H-NMR performed under the same conditions as in Example 1 based on the assumption that the molecular weight of MEK-20T was 20,000. The ratio of the molar number of lactic acid relative to the molar number (1.0) of glycolic acid was 2.4. The resulting PEG-PLGA block copolymer has a structure represented by Formula (VI).

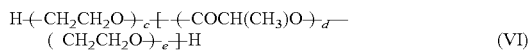

(VI)

In Formula (VI), c is an integer of 200 to 250, d is an integer of 200 to 210, and e is an integer of 80 to 90.

A water-soluble support layer was provided on a PET substrate in the same manner as in Example 1, and a solution prepared by dissolving the PEG-PLGA block copolymer obtained above in dichloromethane at room temperature was applied thereon via gravure coating to provide a 150-nm-thick adhesion prevention layer. The thickness of the adhesion prevention layer was measured in the same manner as in Example 1.

Comparative Example 5

L-lactide (PURASORB® L, manufactured by Corbion) and glycolide (PURASORB® G, manufactured by Corbion) were subjected to random polymerization with each hydroxyl group of linear polyethylene glycol (SUNBRIGHT® DKH-20T, manufactured by NOF Corporation) comprising hydroxyl groups at its ends to synthesize a PLGA-PEG-PLGA block copolymer with the number average molecular weight of approximately 60,000 determined by $^1$H-NMR performed under the same conditions as in Example 1 based on the assumption that the molecular weight of DKH-20T was 20,000. The ratio of the molar number of lactic acid relative to the molar number (1.0) of glycolic acid was 1.8. The resulting PLGA-PEG-PLGA block copolymer has a structure represented by Formula (VII).

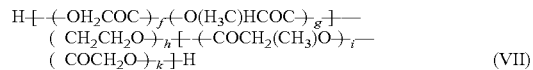

(VII)

In Formula (VII), h is an integer of 200 to 250, g and i are each independently an integer of 300 to 320, and f and k are each independently an integer of 170 to 190.

A water-soluble support layer was provided on a PET substrate in the same manner as in Example 1, and a solution prepared by dissolving the PLGA-PEG-PLGA block copolymer obtained above in dichloromethane at room temperature was applied thereon via gravure coating to provide a 150-nm-thick adhesion prevention layer. The thickness of the adhesion prevention layer was measured in the same manner as in Example 1.

Comparative Example 6

With the use of pullulan and the PET substrate as used in Example 1, a 0.5-μm-thick water-soluble support layer was provided on the PET substrate via gravure coating. The thickness of the support layer was measured in the same manner as in Example 1.

Subsequently, a solution prepared by dissolving the 4 PEG-PLGA block copolymer obtained in Example 2 in ethyl acetate heated to 55° C. was applied on the water-soluble support layer prepared in the manner described above via gravure coating to provide a 150-nm-thick adhesion prevention layer. The thickness of the adhesion prevention layer was measured in the same manner as in Example 1.

Comparative Example 7

With the use of pullulan and the PET substrate as used in Example 1, a 20-μm-thick water-soluble support layer was provided on the PET substrate via casting. The thickness of the support layer was measured in the same manner as in Example 1.

Subsequently, a solution prepared by dissolving the 4 PEG-PLGA block copolymer obtained in Example 2 in ethyl acetate heated to 55° C. was applied on the water-soluble support layer prepared in the manner described above via gravure coating to provide a 150-nm-thick adhesion prevention layer. The thickness of the adhesion prevention layer was measured in the same manner as in Example 1.

In the same manner as in Example 4, the 6,000-μm-thick second water-soluble support layer of an unwoven fabric with the weight per unit area of 1,500 g/m² was provided on a PET substrate via dry spinning. The thickness and the weight per unit are of the second water-soluble support layer were measured in the same manner as in Example 4.

In the same manner as in Example 4, the first water-soluble support layer and the adhesion prevention layer were stripped off from the PET substrate. Pure water was sprayed on the first water-soluble support layer in an amount of 5 g/m² with the use of an accumulator sprayer. Immediately thereafter, the stripped adhesion prevention layer was adhered to the second water-soluble support layer.

2. Solubility Test of Water-Soluble Support Layer (1) Preparation of Test Pieces From the materials for adhesion prevention produced in accordance with Examples 1 to 10 and Comparative Examples 1 to 7, test pieces of areas of 4 cm² were prepared, a water-soluble support layer comprising an adhesion prevention layer was stripped off from the PET substrate, and the water-soluble support layer was positioned on the gas phase side.

(2) Test Method

Solubility of the water-soluble support layer was evaluated in the manner described below. When solubility of a layer of a water-soluble material is examined on the basis of the condition of the support layer and the adhesion prevention layer are stacked on top of the other, the adhesion prevention layer is first removed. Specifically, 12 g of chloroform is introduced into a petri dish (a deep type TPX petri dish, manufactured by SANPLATEC CO., LTD.), the laminate of 5-cm-square samples (hereafter, referred to as a "test piece") was fixed in midair to prevent the layer of a water-soluble material from being soaked in chloroform, and the adhesion prevention layer was soaked in chloroform. Thereafter, the petri dish was hermetically sealed and allowed to stand with heating at 35° C. for 30 minutes, chloroform exchange was carried out approximately 3 times, and the test pieces were removed and air dried. Thus, the adhesion prevention layer was removed.

The distance between the water-soluble support layer of the test piece and the edge of the burette was adjusted to 10 mm. The time point at which a drop of water (about 0.04 ml) at room temperature was dropped from the burette to the surface of the water-soluble support layer is designated as the point of initiation, the time point at which water penetrated through the other surface and the water-soluble support layer is dissolved is designated as the point of termination, and the duration from the point of initiation to the point of termination was measured. When water reached the other surface, the surface from which water was applied dropwise to the water-soluble support layer was gradually dissolved, the shape of the other surface could not be retained, and the water-soluble support layer was dissolved.

Evaluation criteria were as follows:

A: The time required until the completion of dissolving is 15 seconds to less than 3 minutes.

B: The time required until the completion of dissolving is 10 seconds to less than 16 seconds or 3 minutes to less than 5 minutes.

C: The time required until the completion of dissolving is less than 10 seconds or 5 minutes or longer.

(3) Test Results

The test results are summarized in Table 1. The water-soluble support layers of Examples 1 to 4, Examples 6 to 10, and Comparative Examples 1 to 5 were rapidly dissolved; that is, these support layers were excellent in solubility. While the water-soluble support layer of Example 5 tended to dissolved at a slow rate because of an increased thickness of the second water-soluble support layer, it was dissolved within 5 minutes. In contrast, the water-soluble support layer of Comparative Example 6 was dissolved too rapidly because of an excessively small thickness. That is, it was poor in solubility. Concerning the water-soluble support layer of Comparative Example 7, both the first water-soluble support layer and the second water-soluble support layer were thick. Thus, it was not dissolved within 5 minutes. That is, it was poor in solubility.

TABLE 1

| Samples | Evaluation of water solubility |
|---|---|
| Example 1 | A |
| Example 2 | A |
| Example 3 | A |
| Example 4 | A |
| Example 5 | B |
| Example 6 | A |
| Example 7 | A |
| Example 8 | A |
| Example 9 | A |
| Example 10 | A |
| Comparative Example 1 | A |
| Comparative Example 2 | A |
| Comparative Example 3 | A |
| Comparative Example 4 | A |
| Comparative Example 5 | A |
| Comparative Example 6 | C |
| Comparative Example 7 | C |

3. Evaluation of Shape Retainability of Adhesion Prevention Layer in Water

The adhesion prevention layer is used in the body. When shape retainability is poor in water, accordingly, use thereof becomes difficult. Therefore, the samples produced in accordance with Examples 1 to 10 and Comparative Examples 1 to 5 were subjected to evaluation of the adhesion prevention layers concerning shape retainability in water.

(1) Preparation of Test Pieces

From the materials for adhesion prevention produced in accordance with Examples 1 to 10 and Comparative Examples 1 to 5, test pieces of areas of 4 cm² were prepared.

(2) Test Method

Deionized water at room temperature was introduced into a glass petri dish and test pieces were introduced thereinto. The water-soluble support layer was thoroughly dissolved, and changes in the shape of the adhesion prevention layers were observed for a day.

(3) Test Results

The adhesion prevention layers of Examples 1 to 10 and Comparative Examples 1 and 2 were excellent in shape retainability and changes such as fracture or elongation were not observed. In contrast, the adhesion prevention layers of Comparative Example 3 and 4 were fractured immediately after the water-soluble support layer was dissolved. That is, these layers were poor in shape retainability. The adhesion prevention layer of Comparative Example 5 was elongated in a transverse direction and then fractured after the water-soluble support layer was dissolved. That is, the adhesion prevention layer of Comparative Example 5 was also poor in shape retainability. The test results are summarized in Table 2 below.

TABLE 2

| Samples | Shape retainability |
| --- | --- |
| Example 1 | No change |
| Example 2 | No change |
| Example 3 | No change |
| Example 4 | No change |
| Example 5 | No change |
| Example 6 | No change |
| Example 7 | No change |
| Example 8 | No change |
| Example 9 | No change |
| Example 10 | No change |
| Comparative Example 1 | No change |
| Comparative Example 2 | No change |
| Comparative Example 3 | Fracture immediately after dissolution of the support layer |
| Comparative Example 4 | Fracture immediately after dissolution of the support layer |
| Comparative Example 5 | Elongation in transverse direction and fracture immediately after dissolution of the support layer |

4. Evaluation of Degradability of Adhesion Prevention Layer in PBS (1) Preparation of Test Pieces From the materials for adhesion prevention produced in accordance with Examples 1 and 2 and Comparative Examples 1 and 2, test pieces of areas of 250 cm² were prepared. The test pieces were soaked in water to dissolve the support layers, the remaining film-like adhesion prevention layers were washed 3 times with PBS (DPBS, manufactured by Thermo Fisher), and the resultants were soaked in 50 ml of PBS in the end.

(2) Test Method

PBS (50 ml) in which the adhesion prevention layers had been soaked was heated to 37° C. and kept shaken moderately at 50 rpm. The adhesion prevention layers were removed 28 days after the initiation of soaking and subjected to chloroform extraction. The resultants were subjected to vacuum drying overnight and the mass assays were then performed. On the basis of a change in the mass between before and after the soaking in PBS, a percentage of mass change was determined in accordance with (4).

Decrease in mass of material for adhesion prevention (%)=100×{(mass of material for adhesion prevention before soaking)−(mass of material for adhesion prevention after soaking)}/(mass of material for adhesion prevention before soaking)　　　(4)

(3) Test Results

The test results are summarized in Table 3 below. Since the adhesion prevention layers of Examples 1 and 2 comprising PEG introduced thereinto had improved hydrophilicity as a result of PEG introduction, these layers were excellent in terms of the rate of hydrolysis, and a percentage of mass decrease 28 days after the initiation of soaking was 60% or higher. In contrast, the adhesion prevention layers of Comparative Examples 1 and 2 were poor in terms of the rate of hydrolysis, and a percentage of mass decrease 28 days after the initiation of soaking was low. This indicates that these layers would remain in the body for a long period of time.

TABLE 3

| Samples | Decrease in mass after soaking in PBS at 37° C. for 28 days (%) |
| --- | --- |
| Example 1 | 61 |
| Example 2 | 65 |
| Comparative Example 1 | 4 |
| Comparative Example 2 | 26 |

5. Evaluation of Capacity for Adhesion Prevention Using Mice (1) Preparation of Test Pieces From the materials for adhesion prevention produced in accordance with Examples 1 and 2 and Comparative Examples 1 and 2, samples of areas of 4 cm² were prepared, and the samples were cut into pieces of 1 cm² to prepare test pieces for the adhesion prevention test.

(2) Test Method

Mice (C57BL/6, females, 12- to 15-week-old) were subjected to an abdominal operation under general anesthesia via an abdominal midline incision of about 2 cm to expose the digestive canal. Subsequently, the abdominal wall on one side was lifted with the use of clamps to prepare a peritoneal defect of φ 5 mm. Thereafter, one end of the appendix was sutured with the defect by hauling an area within 1 mm from the defect to provide the appendix in close contact with the peritoneal defect. The test piece stripped off from the PET substrate was provided in an area between the appendix and the peritoneal defect, the support layer was dissolved with 0.5 ml of physiological saline, and the resultant was provided in the defect (the group subjected to adhesion). The abdominal wall on the other side was also subjected to the same procedure to prepare the peritoneal defect, the digestive canal was brought back to the original position in the body without adhering the test piece, and the abdomen was closed using an absorbable surgical suture (the group not subjected to adhesion). Concerning each of the samples according to Examples 1 and 2 and Comparative Examples 1 and 2, at least 7 mouse models of adhesion were prepared.

(3) Evaluation of Adhesion Score

Mouse models of adhesion were sacrificed via cervical dislocation 7 days after the preparation, the abdomen was opened to collect the peritoneal defect, and adhesion scores were visually evaluated on the basis of the given standard. Adhesion was evaluated in terms of a 5-point scale of 1 to 5 indicated below concerning stripping of the adhesion site:

Score 1: No adhesion
Score 2: Some adhesion easily stripped by gravity
Score 3: Need of blunt stripping
Score 4: Need of sharp stripping
Score 5: Tissue loss at the time of stripping.

(4) Evaluation Results

The results of evaluation are summarized in Table 4 and in the chart in FIG. 1. In the Examples and Comparative Examples, significant differences in average adhesion scores were assessed between the group subjected to adhesion and the group not subjected to adhesion. The Mann-Whitney U test was used to assess for significant differences and the Ryan's method was used to perform multiple comparison. In addition, significant differences were assessed between Examples and Comparative Examples.

As a result of the significant difference test, significant differences were observed in all the groups of Examples 1 and 2 and Comparative Examples 1 and 2 and between the group subjected to adhesion and the group not subjected to adhesion. In addition, no significant differences were observed between Examples and Comparative Examples, and all the test pieces were found to exert equivalent capacities for adhesion prevention.

TABLE 4

| Samples | Average adhesion score | |
|---|---|---|
| | Group subjected to adhesion | Group not subjected to adhesion |
| Example 1 | 1.5 | 3.5 |
| Example 2 | 1.4 | 2.7 |
| Comparative Example 1 | 1.8 | 4.0 |
| Comparative Example 2 | 1.4 | 3.7 |

Figure 2:
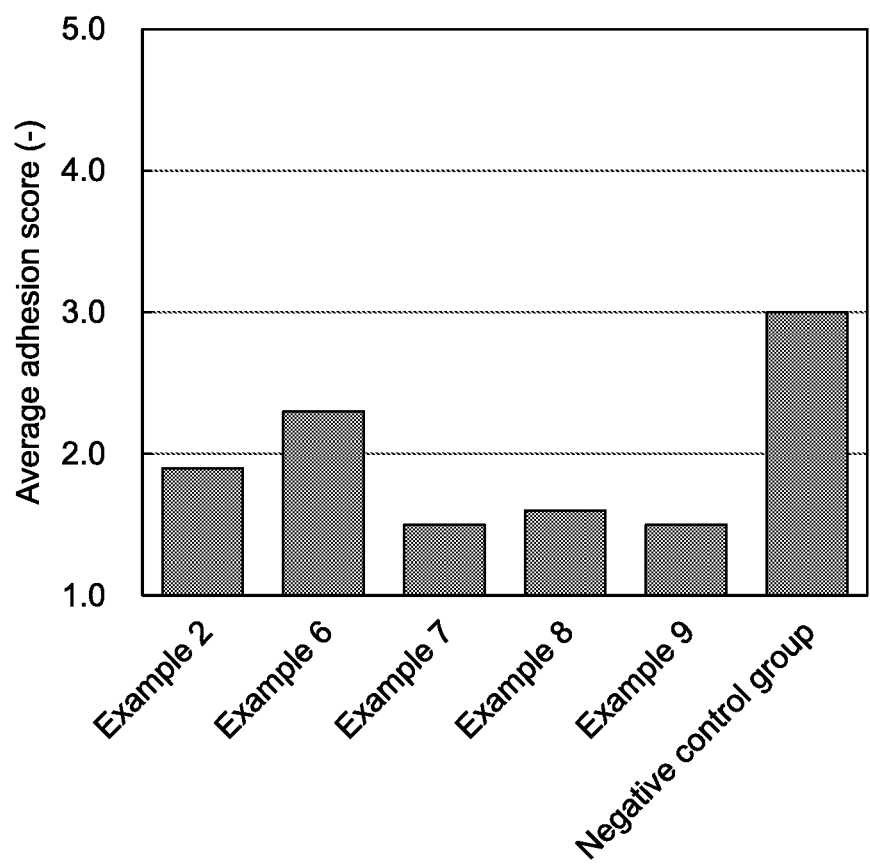
FIG. 2 shows a chart demonstrating the results of evaluation of the materials for adhesion prevention of Examples 2 and 6 to 9 and a negative control group concerning the ability for adhesion prevention using rats.

6. Evaluation of Capacity for Adhesion Prevention Using Rats
(1) Preparation of Test Pieces From the materials for adhesion prevention produced in accordance with Examples 2 and 6 to 9, samples with areas of 9 cm² were prepared as test pieces for the adhesion prevention test.
(2) Test Method Rats (Crl:CD (SD), males, 6- to 7-week-old) were subjected to an abdominal operation under general anesthesia via an abdominal midline incision of about 3 to 4 cm to expose the appendix. Subsequently, areas of about 2 cm² on the small intestine side of the exposed appendix were abraded with sterile gauze until dot hemorrhage occurred. The test pieces were provided in the abrasion sites, the support layer was dissolved with 0.5 ml of physiological saline, and the resultant was provided in the defect (the group subjected to adhesion). The appendix was brought back to the original position in the body, and the abdomen was closed using an absorbable surgical suture. Concerning each of the samples according to Examples 2 and 6 to 9, 8 mouse models of adhesion were prepared. As a negative control group, a group to which the test substance would not be adhered was prepared.
(3) Evaluation of Adhesion Score Rat models of adhesion were sacrificed via bleeding under anesthesia 14 days after preparation and adhesion scores at the adhesion-induced sites were evaluated. Adhesion was evaluated in terms of a 5-point scale of 1 to 5 indicated below:
Score 1: No adhesion
Score 2: Small adhesion easily separated
Score 3: Weak adhesion resistant to mild tugging in a narrow range
Score 4: Firm adhesion or adhesion in at least 2 sites
Score 5: Adhesion in 3 or more sites.
(4) Results of Evaluation The results of evaluation are summarized in Table 5 and in the chart shown in FIG. 2. Adhesion scores were lowered, compared to those of negative controls of Examples 2 and 6 to 9, and these examples were found to exert usefulness as the materials for adhesion prevention.

TABLE 5

| Samples | Average adhesion score |
|---|---|
| Example 2 | 1.9 |
| Example 6 | 2.3 |
| Example 7 | 1.5 |
| Example 8 | 1.6 |
| Example 9 | 1.5 |
| Negative control group | 3.0 |

INDUSTRIAL APPLICABILITY

Our material for adhesion prevention is excellent in biodegradability. Even if it is indwelled in the body, accordingly, it would be degraded at an early stage. That is, such material is excellent in safety. In addition, such material can be easily applied to damaged areas of biological tissues that are in need of prevention or reduction of adhesion. Accordingly, usefulness thereof as a material for adhesion prevention can be very high in the field of medicine.

All publications, patents, and patent applications cited herein are incorporated herein by reference in their entirety.

This description includes part or all of the content as disclosed in JP 2016-194699, the priority of which is claimed.

The invention claimed is:

1. A material for adhesion prevention composed of a 1 to 1,000 μm-thick water-soluble support layer comprising a water-soluble polymer and a 10 to 1,000 nm-thick adhesion prevention layer comprising a biodegradable polymer, wherein the biodegradable polymer is composed of a branched polyalkylene glycol comprising 4 terminal hydroxyl groups per molecule bound to a polyhydroxy alkanoic acid and the mass ratio of the branched polyalkylene glycol relative to the total mass is 1% to 40%,
wherein the biodegradable polymer has a structure represented by Formula (I):

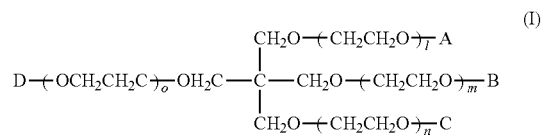

wherein, l, m, n, and o are each independently an integer of 24 to 88 and A, B, C, and D each independently represent a group represented by Formula (II):

wherein, x is an integer of 90 to 148 or a group represented by Formula (III):

wherein, y is an integer of 72 to 132 and z is an integer of 19 to 39; and
wherein the polyhydroxy alkanoic acid in the biodegradable polymer represented by Formula (I) is a copolymer of lactic acid and glycolic acid and a ratio of the molar number of the lactic acid relative to the molar number of the glycolic acid in the biodegradable polymer is 3.0 to 5.0.

2. The material according to claim 1, wherein the water-soluble polymer is a polysaccharide or modified polysaccharide.

3. The material according to claim 1, wherein the water-soluble polymer is selected from the group consisting of pullulan, hyaluronic acid, acylated pullulan, acylated hyaluronic acid, acetylated pullulan, acetylated hyaluronic acid, and a mixture of two or more thereof.

4. The material according to claim 1, wherein the support layer is provided on a substrate, the support layer is adhered to the substrate with a strength that can be stripped off from the substrate, and the adhesion prevention layer is provided on the support layer.

* * * * *